United States Patent [19]

Weissman et al.

[11] 3,989,088

[45] Nov. 2, 1976

[54] CASTING MACHINE AND IMPROVED CONTROL CIRCUIT FOR OPERATION

[75] Inventors: Bernard Weissman, New York, N.Y.; Max Schneiderman, Clifton, N.J.; Alan N. Miller, New City, N.Y.

[73] Assignee: IPCO Hospital Supply Corporation (Whaledent International Division), New York, N.Y.

[22] Filed: Dec. 29, 1975

[21] Appl. No.: 645,093

[52] U.S. Cl. ............................... 164/157; 164/256; 164/DIG. 4; 164/284
[51] Int. Cl.$^2$........................................... B22D 17/32
[58] Field of Search ........... 164/157, 254, 255, 256, 164/257, 258, DIG. 4, 120, 62, 65, 285, 335, 253, 284

[56] References Cited

UNITED STATES PATENTS

| 1,703,739 | 2/1929 | Kelpsch | 164/256 X |
| 3,690,367 | 9/1972 | Daniels | 164/258 X |
| 3,705,615 | 12/1972 | Watts | 164/65 X |

FOREIGN PATENTS OR APPLICATIONS 502,266   11/1954   Italy ..................................... 164/254

*Primary Examiner*—Ronald J. Shore
*Attorney, Agent, or Firm*—Friedman, Goodman & Teitelbaum

[57] ABSTRACT

A casting machine including a control circuit which automatically controls its operation. The casting machine includes a casting chamber which supports an alloy filled open-ended container whose open end faces the sprue hole of an investment casting ring. The control circuit couples a vacuum to the casting chamber while maintaining the casting chamber in its initial upright position. After a first timing interval, the chamber is inverted and the vacuum is decoupled from the casting chamber, and compressed air is applied to the casting chamber. After a second subsequent time interval the casting chamber is automatically returned to its initial upright position, the action of which causes the casting chamber to be automatically vented to the atmosphere.

20 Claims, 13 Drawing Figures

VACUUM

CASTING

PRESSURE

3,989,088

CASTING MACHINE AND IMPROVED CONTROL CIRCUIT FOR OPERATION

BACKGROUND OF THE INVENTION

1. Field of the Invention

This invention relates to casting machines and more particularly to an automatically controlled casting machine of the type which produces metal casts, as for example dental casts.

2. Description of the Prior Art

Casting machines are used for the casting of perfect metal casts, as is needed in various fields of technology, such as dentistry. Such casting machines are presently available, as for example, the Chronomatic System I Casting Machine marketed by the Whaledent International Co., N.Y., N.Y. Such casting machines contain a casting chamber which can support an alloy filled, open-ended container and an investment casting ring having a sprue hole. The sprue hole is positioned above the open end of the container. The casting chamber contains a handle which is manually manipulated. While held in an initial upright position, a vacuum is introduced into the casting chamber. After a while the casting chamber is manually inverted permitting the alloy to flow into the mold in the investment ring. Simultaneously, the vacuum is terminated and instead compressed air is allowed to flow into the casting chamber. The casting chamber is maintained in its inverted position, and after a while, is again manually returned to its initial upright position while being vented to the atmosphere.

However, the prior art machine is extremely sensitive to errors and poor casts have been formed. For example, an extremely critical step is the turning of the casting chamber. If the chamber is turned too slowly, an incomplete cast is formed. If the casting chamber is turned too abruptly, the alloy will be spilled. If the venting takes place too quickly, the upper button of the sprue hole will be broken off and the sprue will be hollow. Additionally, if the setting time under pressure is too short or the setting time under compressed air is improper, the cast will also be faulty and of improper shape. Also, an incomplete casting can occur if the vacuum is too weak, the pressure too low, or the solidification time too short. A short solidification time will also cause shrinkage in the casting resulting in holes near the sprue entrance.

Because of the critical timing for the turning of the casting chamber as well as the criticality of the vacuum and pressure time intervals, the numerous imperfections and faults in the resulting casts have made the process an extremely expensive one and frequently requires numerous recasts to produce the final high quality cast needed.

SUMMARY OF THE INVENTION

It is accordingly an object of the present invention to provide an improved casting machine which avoids the aforementioned problems of prior art casting machines.

Another object of the present invention is to provide a control device which can be attached to prior art casting machines to automatically control the operation thereof, and thereby avoid the aforementioned problems in prior art casting machines.

Yet a further object of the present invention is to provide an improved casting machine which will automatically turn a casting chamber after a predetermined interval of vacuum has been applied to the casting chamber, and will automatically return the casting chamber to its initial position after a subsequent predetermined interval during which pressure has been applied to the casting chamber.

Yet another object of the present invention is to provide a casting machine which will automatically turn a casting chamber at a constant uniform speed.

A further object of the present invention is to provide a casting machine which will automatically carry out the steps of, applying a vacuum to a casting chamber, inverting the casting chamber, terminating the vacuum, applying compressed air to the casting chamber, returning the casting chamber to its initial position after the cast has solidified under pressure, and venting the casting chamber to the atmosphere.

Yet a further object of the present invention is to provide a casting machine which includes a motor or like device for automatically turning the shaft of a casting chamber and which further includes a brake mechanism which locks the casting chamber in its initial upright position.

These and other objects, features and advantages of the invention will, in part, be pointed out with particularity, and will, in part, become obvious from the following description of the invention, taken in conjunction with the accompanying drawings, which form an integral part thereof.

Briefly, the invention comprises a casting machine having a rotatable casting chamber having a hermetically sealable lid, the casting chamber being capable of supporting an alloy filled, open-ended container, and an investment casting ring having a sprue hole. In the casting chamber, the spure hole is positioned over the open end of the container. A vacuum means produces a vacuum in the casting chamber, while a pressure means is available for providing compressed air into the casting chamber, and a venting means is provided for venting the casting chamber. A casting control circuit is also provided which includes an energizing switch means for activating the vacuum means. The control circuit also includes a vacuum timing means which is activated by the energizing switch means for decoupling the vacuum means from the casting chamber after a first predetermined time interval. A motor means is also included in the control circuit and is connected to the casting chamber, the motor means is activated by the termination of the first time interval to thereby rotate the casting chamber to an inverted position. The control circuit also includes a pressure timing means, which is activated by the termination of the first timing interval and interconnects the pressure means to the casting chamber for a subsequent second predetermined time interval. The motor means is also activated by the termination of the second time interval to thereby return the casting chamber to its initial upright position. A reversing switch, also included in the control circuit, is activated by the termination of the second timing interval for interconnecting the venting means to the casting chamber.

In another embodiment, the control circuit is provided as an attachment to existing casting machines and can be mechanically and electrically coupled thereto.

BRIEF DESCRIPTION OF THE DRAWINGS

In the drawings.

In the various figures of the drawing, like reference characters designate like parts.

DESCRIPTION OF THE PREFERRED EMBODIMENT

Figure 1:
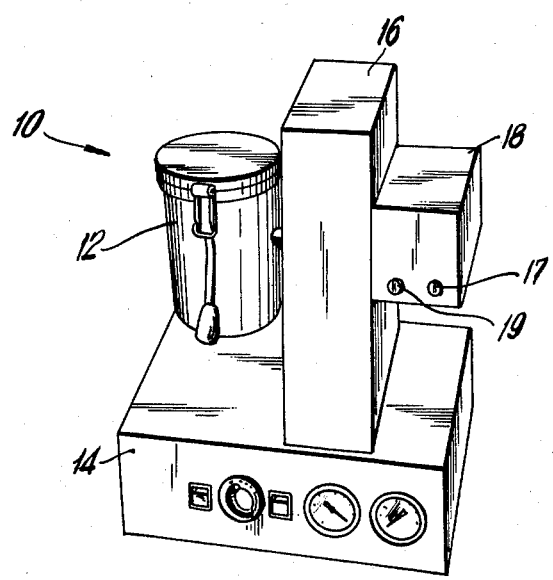
FIG. 1 shows an isometric view of the casting machine in accordance with the present invention.

Referring now to FIG. 1 there is generally shown the casting machine of the present invention 10 which includes a casting chamber 12, a base section 14 containing a substantial amount of the circuitry, gages and switches needed in the operation of the casting machine, and an upright section 16 which supports the casting chamber and provides the interconnection between the casting chamber and the base section 14. A control section 18 is connected to the upright section 16 and interconnects to the casting chamber. The control section 18 includes the necessary circuitry and motors for automatically carrying out the operation of the casting machine. Dials 17 and 19 are externally available for respectively controlling the pressure time interval and the vacuum time interval.

Although FIG. 1 shows an entire automatic casting machine in accordance with the present invention, the present invention also contemplates the provision of the control section 18 as an attachment to existing casting machines wherein the section 18 is mechanically and electrically interconnected to provide automatic control of existing casting machines.

Figure 2:
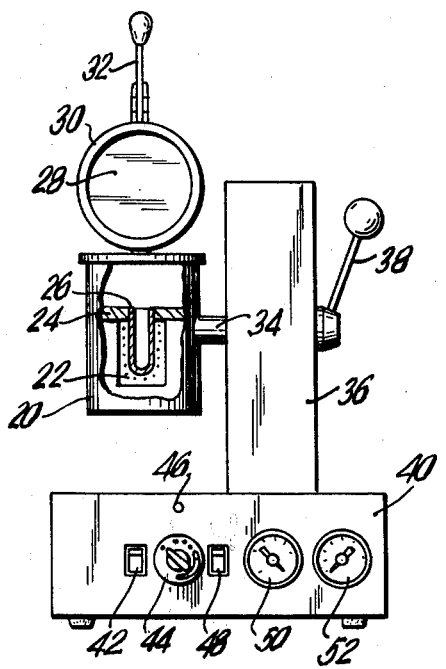
FIG. 2 is a front view of a prior art casting machine.
Figure 3:
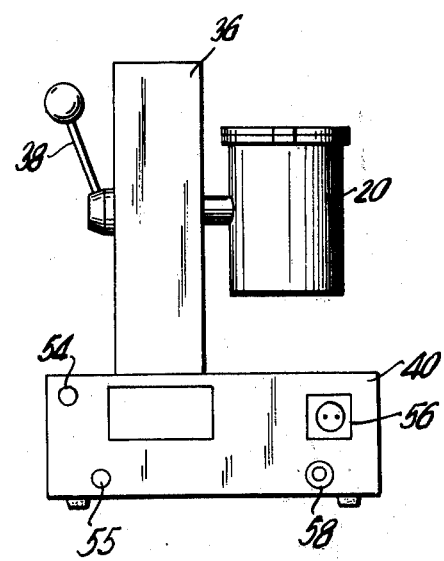
FIG. 3 is a rear view of a prior art casting machine.

Referring now to FIGS. 2 and 3 there will be described the pertinent sections of the prior art casting machines. The casting chamber 20 includes therein a heating element 22, with a support plate 24 positioned at the top of the heating element and capable of supporting a cylinder 26, usually a ceramic crucible, which forms part of the heating element. The crucible is inserted with its open end facing upward. The lid 28 is hinged to the casting chamber and contains thereon an asbestos disk. A seal ring 30 is provided to completely hermetically seal the lid onto the chamber, and a quick release lid lock 32 is included to close the lid onto the chamber.

The casting chamber 20 is supported by a support section 36 by means of a shaft 34 holding the chamber and passing through the section 36 to a manually manipulatable rotating arm 38. By means of the rotating arm the casting chamber can be manually inverted and then returned to its initial upright position.

In the base section 40 there is contained the necessary mechanical and electrical equipment for carrying out the casting process. Externally thereon is contained various switches, gauges and indicator bulbs for controlling the operation. Switch 42 turns on the heating element 22 contained in the casting chamber and by means of the temperature control knob 44 the desired temperature in the casting chamber is controlled. The indicator lamp 46 provides a visual indication of the operation of the heating element in the casting chamber. The main switch for the casting operation is provided by means of switch 48. Gauge 50 provides a visual indication of the vacuum being applied to the casting chamber while gauge 52 provides visual indication of the pressure provided by the compressed air pump.

On the rear of section 40 is provided a connection 54 for the application of a compressed air pump, and a connection 55 for a vacuum pump. The vacuum pump can be electrically interconnected to the casting machine through the plug 56 to be energized thereby. A fuse 58 is available to prevent electrical damage to the casting machine.

Figure 4A:
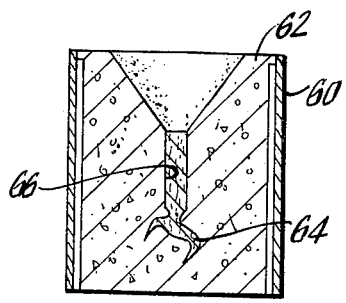
FIG. 4A–4F show steps in the operation of the casting machine.

Referring now to FIGS. 4A–4F, there will be explained the operation of the prior art casting machine. As shown in FIG. 4A, initially there is provided a wax mold 64 of desired cast. For example, in dentistry, the wax mold will be the shape of a particular tooth or groups of teeth. The wax mold is made with a sprue 66 connected thereto, and is placed in a casting ring 60 with investment 62 placed about the wax mold and within the casting ring. The casting ring is then heated to melt the wax pattern and provide a sprue hole and mold cavity in the investment ring.

Figure 4B:
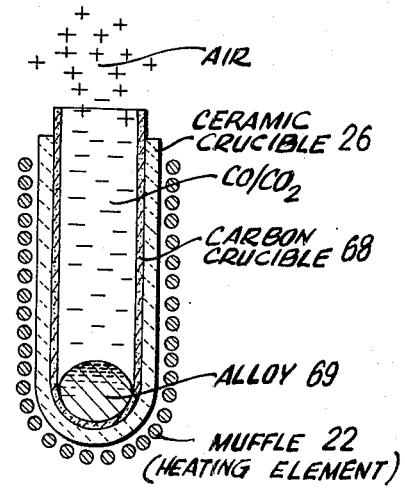

The alloys utilized for providing the cast are also initially prepared in a container. As shown in FIG. 4B, the alloys are generally melted in a carbon crucible 68 whereby only oxides of carbon are formed during the red hot stage of melting. The carbon crucible 68 is inserted into the ceramic crucible 26 when the ceramic crucible 26 has turned red or white hot. Then, the alloy 69 is placed into the carbon crucible 68 and properly melted.

The vertical orientation of the crucible permits it to be filled with the carbon monoxide and carbon dioxide layer, which is heavier than air. This protective gas layer isolates the molten metal and prevents mixing with the undesirable atmospheric oxygen even by convection currents.

Figure 4C:
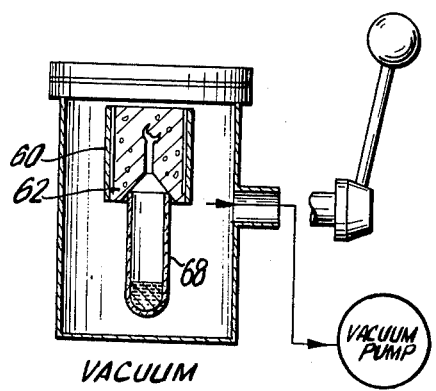

As shown in FIG. 4C, the preheated investment casting ring 60 is placed in the casting chamber over the carbon crucible 68 containing the melted alloy, with the sprue hole facing down such that it faces the open end of the carbon crucible 68. The lid is closed and the casting chamber is manually held by the rotating arm in its upright position. A vacuum pump is coupled to the casting chamber, to assure a well degassed alloy. The gases are eliminated from the casting ring which prevents the formation of porosities when gases are entrapped into the solidifying metal.

Figure 4D:
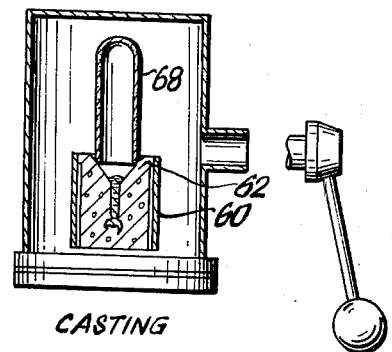

In order to carry out the casting operation, the casting chamber is manually rotated to an inverted position by means of the rotating arm, as shown in FIG. 4D. As a result, the melt flows due to gravity into the vacuum evacuated mold.

Figure 4E:
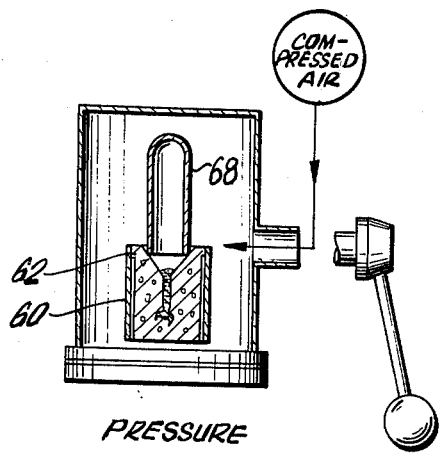

Compressed air is then coupled to the casting chamber to provide therein an increased pressure, as shown in FIG. 4E. Initially, the alloy travels slowly enough to allow all debris, which is of low specific gravity, to flow to the top. Because of this phenomenon, crowns, inlays, etc. are cast without inclusions as a consequence of the foreign matter having been deposited on the casting button. When compressed air is quickly admitted into the casting chamber at precisely the correct instant, the alloy is forced into all fine margins of the cast and even though the precious metals being used have a high surface tension, thin walled crowns and fine margins can be reproduced.

Figure 4F:
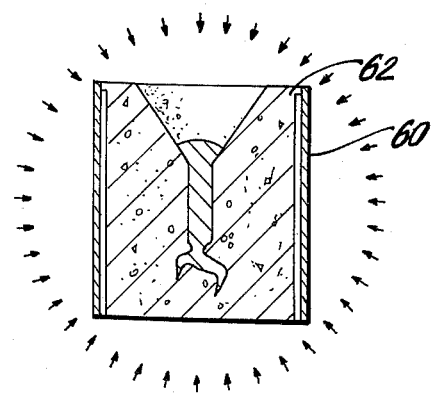

As shown in FIG. 4F, the pressure is exerted equally on all surfaces. By changing from vacuum to pressure phases, an effective pressure differential of approximately 60 PSI can be provided. Because the pressure acts equally on all surfaces, the risk of breaking through the investment top is eliminated. The alloy is allowed to solidify under pressure.

Following the setting of the alloy, the vacuum pump is switched off and the casting chamber is manually vented to the atmosphere, and then manually turned back to its initial upright position. Then, the casting can be removed from the chamber.

The turning of the casting chamber from its initial upright position to its inverted position is a most critical step in the operation. It is during this step that the alloy flows into the casting mold and it is during this step that faults most frequently are introduced into the cast. By turning the casting chamber too slowly or too quickly, an incomplete cast can be produced; the alloy can be spilled; the button can be broken off with the sprue remaining hollow, and shrinkage can occur in the casting. Additional critical steps in the casting operation relate to the proper timing cycles for the vacuum and pressure phases. Since these various steps are all interrelated, constant manual attention must be given to the casting machine and only through great experience and attention can a high quality cast be produced.

Figure 5:
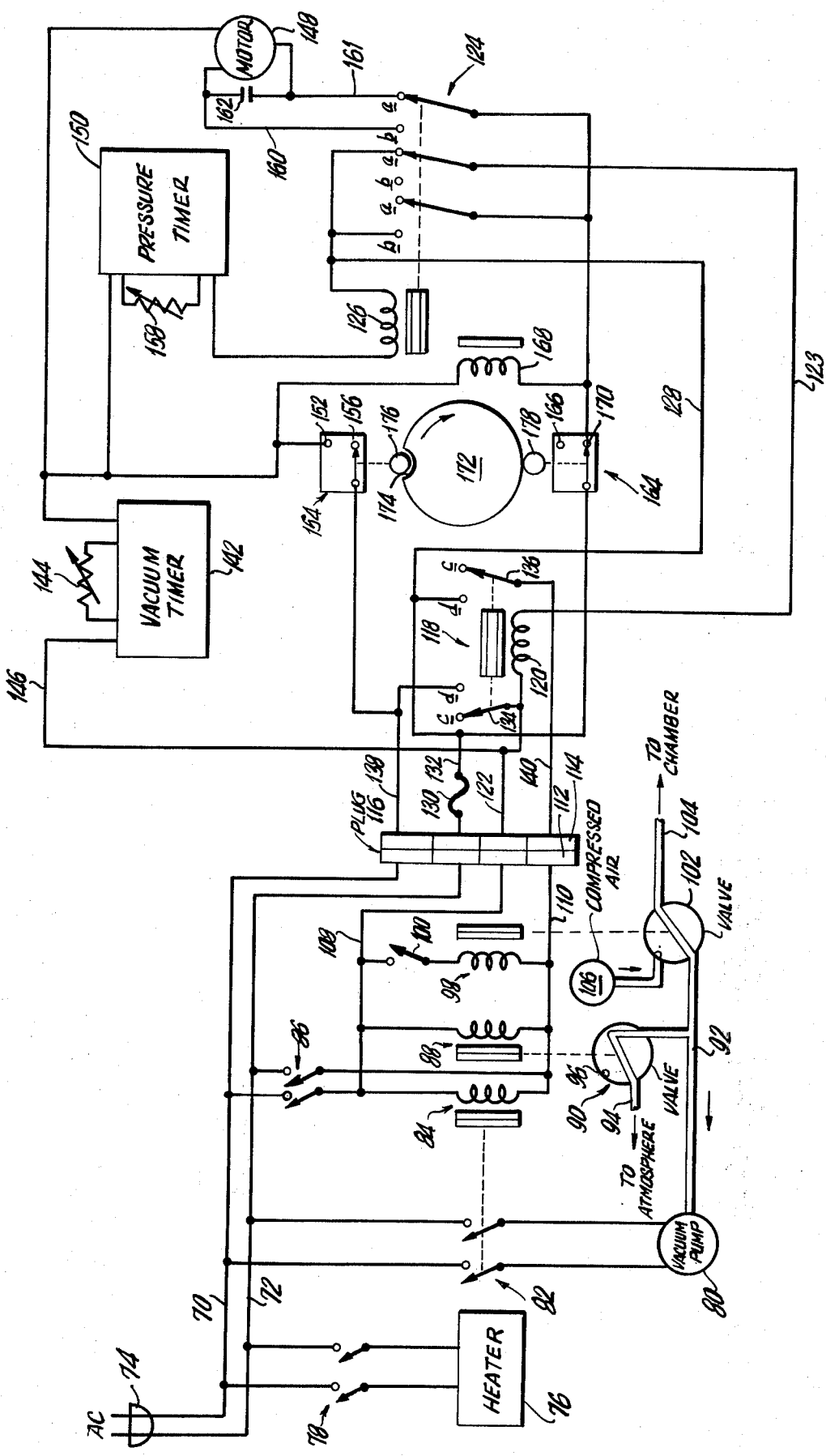
FIG. 5 is a circuit diagram for carrying out the automatic control of the casting machine, in accordance with the present invention.

Referring now to FIG. 5, there will be shown a control circuit which can automatically provide the heretofore described casting process and can eliminate the errors introduced by improper turning of the chamber and improper timing of the casting process. The main power lines 70, 72 are adapted to be interconnected to an AC source by means of the plug 74. The heater 76 is interconnected to the main power lines by means of the switch 78. Also connected across the main power lines 70, 72 is a vacuum pump 80 which is interconnected by means of the switches 82 controlled by the coil of a relay switch 84. The relay switch 84 is connected to lines 108, 110 which are connected across the main power lines 70, 72 by means of a momentary contact switch 86. Also connected in parallel across the lines 108, 110 is a further solenoid coil 88 which controls the operation of a valve 90 having a first position interconnecting a tubing 92 to the atmosphere 94 and a second position 96 interconnecting the tubing 92 to a dummy connection. A further solenoid coil 98 is also connected in parallel across the lines 108, 110 and is connected in series with a switch 100 operated by the turning of the casting chamber to its inverted position. The solenoid coil 98 controls valve 102, having a first position interconnecting the main tube 104 leading to the casting chamber with the tubing 92, and having a second position interconnecting the main tubing 104 to a source of compressed air 106. The main power lines 70, 72 as well as the parallel lines 108, 110 are fed to a female socket 112 which is part of an interconnecting plug shown generally at 116, the other part being the male plug 114.

The portion shown to the left of the plug 116 essentially exists within the prior art casting machines, with the exception that the switch 86 in the present invention is a momentary contact switch rather than a permanent ON-OFF switch as in prior art casting machines.

The automatic control circuit shown to the right of the plug 116 is adapted to interconnect to the male portion 114 of the plug such that the control circuit can be easily electrically interconnected to existing casting machines by merely inserting the male plug 114 into the female socket 112. The control circuit includes a self-holding relay shown generally at 118 and including a relay coil 120 whose one end interconnects to line 122 which is connected to the plug 114, and whose other end passes through line 123 and to the position $a$ of the ganged switch 124 which is controlled by the relay coil 126. It then passes through lines 128 and line 132 through the fuse element 130 to the plug 114.

The relay coil 120 operates two switches 134 and 136. In the de-energized position, the switches 134, 136 are positioned on dummy contacts $c$. When coil 120 is energized by momentary closure of the switch 84, the switch 134 moves to contact $d$ thereby interconnecting line 122 with line 138. Switch 136 is also moved to its position $d$ which interconnects line 132 with line 140, and the coil 120 voltage is thus maintained to hold the relay 118 in its activated mode.

Vacuum timer 142 contains a normally open switch and can be preset by resistor 144 to time a first predetermined interval whereupon its normally open switch closes. One end of the vacuum timer is connected to line 122 along line 146. The other end of the vacuum timer interconnects to a motor 148, a pressure timer 150 and one contact 152 of a microswitch 154. The other terminal 156 of the microswitch 154 is a dummy terminal. The input to the microswitch is connected through line 138.

The pressure timer 150 also includes a normally open switch and after a predetermined interval, which can be preset by means of adjusting resistor 158, closes the switch to interconnect the timer to the relay coil 126 which causes the switch 124 to move to its position $b$. The motor 148 is connected to the $a$ and the $b$ terminals along lines 160 and 161. Capacitor 162 is connected across the motor output.

A second microswitch 164 is also interconnected between the position $a$ of the ganged switch 124 and line 132. The microswitch 164 contains a dummy contact 166.

A solenoid 168 has one end connected to the output of the vacuum timer 142, which is also connected to the terminal 152 of the microswitch 154. The other end of the solenoid 168 connects to the terminal 170 of microswitch 164. The motor 148 is physically connected to the casting chamber through a shaft represented symbolically at 172. The outer peripheral surface of the shaft 172 contains a detent 174. Switch 154 contains a cam follower 176 and switch 164 contains a cam follower 178. Both cam followers control the operation of their respective switches and cause them to respectively operate when they engage the detent 174. When the casting chamber is in its initial upright position, cam follower 176 engages the detent 174 to keep the microswitch 154 on contact 156. Similarly, when the casting chamber is in its inverted position, the cam follower 178 will engage the detent 174 permitting the switch 164 to be in contact with position 166.

Figure 6:
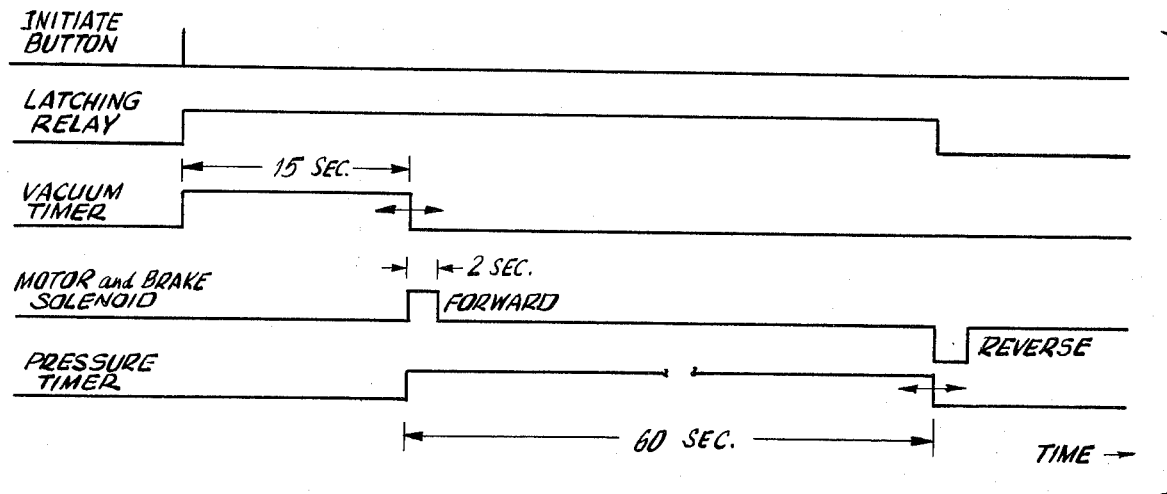
FIG. 6 is a timing diagram for use in explaining the operation of the circuit shown in FIG. 5.

The operation of FIG. 5 will be understood when viewed in conjunction with the timing diagram shown in FIG. 6. When commencing the casting operation, the momentary contact switch 86 is closed. The lines 108, 110 will be placed in parallel with the main lines 70, 72, and through the plug 116 the relay 120 will be energized by current passing through line 122, coil 120, line 123, switch 124 on position *a*, line 128, line 132, through the plug 116 and directly to the line 72. By energizing the coil 120 the switches 134 and 136 will be placed on their *d* position. When in that position, the line 138 is maintained connected to line 122 and the line 130 is maintained connected to the line 140 thereby holding lines 108 and 110 on the left side of switch 116 in energized state to keep the coils 84, 88 energized. As a result, even though the momentary switch 86 will be released, the relay will be maintained energized and will keep lines 180 and 110 activated. The relay 84 will activate the vacuum pump, and the relay coil 88 will cause the valve 90 to move to its dummy position 96. Since the switch 100 is open, coil 98 will not be energized and the valve 102 will interconnect the casting chamber line 104 to the vacuum pump line 92 whereby the casting chamber will be evacuated by means of the vacuum pump 80.

Simultaneously with the latching of the relay 118, the vacuum timer 142 will begin its timing cycle by means of current passing thereto on line 146. After a vacuum timing interval, by way of example 15 seconds, the vacuum timer will close its internal switch thereby energizing the motor 148 by having current passing through the position *a* of the switch 124, through the terminal 170 on microswitch 164, and back through lines 132 and to main power line 72. At the same time, current will also pass through the solenoid 168 and follow the same path back to supply, whereby the solenoid will be energized to release the brake. The motor 148 will cause the casting chamber to begin rotating from its initial upright position. As it rotates, the cam follower 176 will be moved out of the detent 174 to cause the microswitch 154 to move onto position 152 which directly connects the brake solenoid 168 and motor 148 to the main power supply through lines 138 and 70 while simultaneously re-setting the vacuum timer 142.

The casting chamber continues to rotate until it is completely inverted wherein the cam follower 178 will enter into the detent 174. This will cause the microswitch 164 to move to position 166 which disconnects the return line to the power supply and thereby stops the motor 148 and simultaneously releases the solenoid 168. As a result, when the casting chamber reaches its inverted position, the motor will stop. A conventional mechanical stop (not shown) associated with the motor prevents the motor from overshooting the inverted position when the motor is turned off. As shown in FIG. 6, the turning operation will take approximately two seconds and because it is under control of a motor it will be continuous steady turning operation.

Simultaneously with the turning of the casting chamber 172, the switch 100 will be closed thereby energizing the coil 98 and causing the valve 102 to change its position interconnecting the compressed air source 106 to the casting chamber line 104. When the vacuum timer 142 closes, it also begins the timing cycle of the pressure timer 150. The pressure timer continues timing for approximately 60 seconds at the conclusion of which it will energize the coil 126 causing the switches 124 to move to their respective *b* positions. The effect of this movement will be to de-energize the coil 120 by disconnecting the line 123 from the power source. At the same time, the pressure timer will energize the motor 148 by having current pass through the motor from microswitch 154. The current will flow through the switch 124 at position *b* and then back down through the left most part of switch 124 and into line 128, the line 132 and the main power line 72. Also, the brake solenoid 168 will be energized by having current pass througe it and then through the same lines as the motor and back to the power source.

Since the relay 118 is de-energized, lines 122 and 140 are no longer connected to the power supply whereby the coil 84 will be de-energized thereby stopping the vacuum pump and the coil 88 will be de-energized thereby permitting the valve 90 to move back to its position 94 interconnecting it to the atmosphere. Also, coil 98 will be de-energized thereby causing the valve 102 to connect the line 104 to the line 92. As a result, the casting chamber will be connected to the atmosphere permitting it to be vented.

De-energizing of the relay 118 also de-activates line 146 feeding the vacuum timer 142. However, the motor and brake solenoid will now be energized directly through the microswitch 154 which is in position 152. As a result, the motor will now cause the casting chamber to rotate in the reverse direction back to its initial upright position. As the cam follower 78 is taken out of the detent, it restores the microswitch 164 back to its position 170 to make it ready for the next operating cycle. When the casting chamber returns to its initial upright position, the cam follower 176 will enter the detent 174 causing the microswitch 154 to move to position 156 thereby disconnecting the motor and solenoid from the power source and terminating the movement of the casting chamber and at the same time stopping the operation of the motor.

It will therefore be seen that with the control circuits heretofore described, the operation of the rotation is carried out in a smooth consistent manner, and the timing phases are carried out accurately and with precision.

Figure 7:
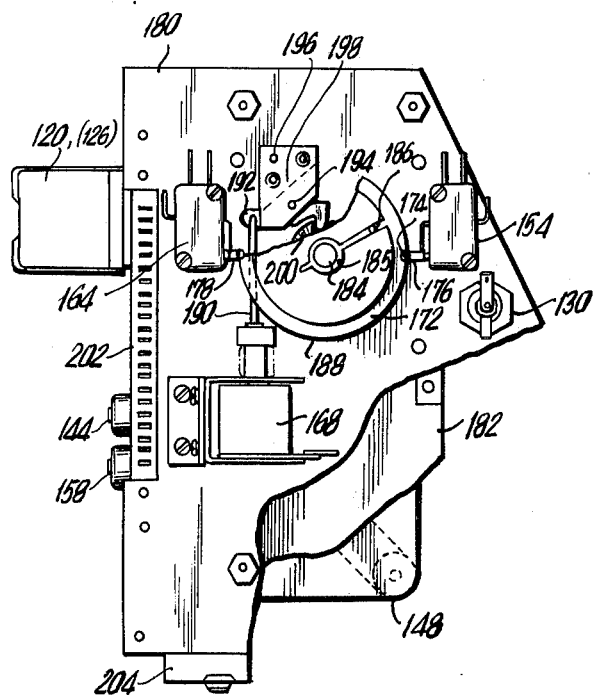
FIG. 7 shows a partially cutaway view of the plate assembly including part of the circuit shown in FIG. 5.

Referring now to FIG. 7 there is shown the plate assembly containing some of the control circuitry heretofore described. On the reverse side of the plate is contained the motor 148 whose output shaft is interconnected by a gear assembly 182 to the gear output shaft 184 which is interconnected to the shaft of the casting chamber. An adapter 172 is securely coupled to the shaft of the casting chamber by means of a set screw 186 which determines the size or clamping fit of the central opening 185 provided in the adapter 172 into which the casting chamber shaft is inserted and secured. The adapter 172 is securely coupled to the shaft 184 by conventional means, such as by a pin (not shown) passing through the adapter and the shaft 184. The adapter 172 contains the outer cam surface 188 containing the detent 174. The microswitches 154 and 164 have their respective cam followers 176, 178 positioned to enter the detent 174.

Figure 8:
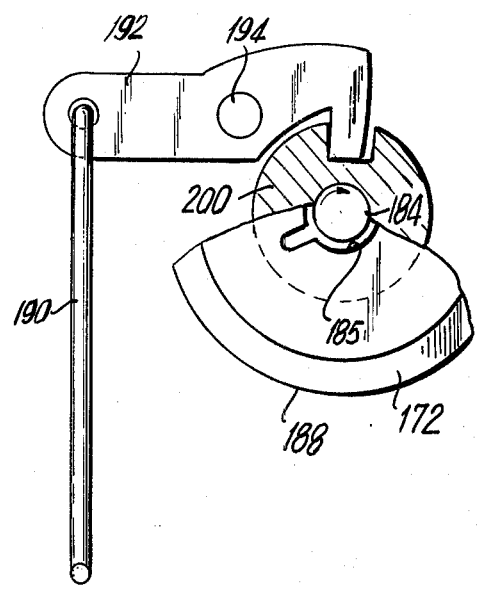
FIG. 8 is a top view of part of the brake assembly shown in FIG. 7.

The brake assembly for locking the casting chamber in its upright position includes the solenoid 168 having a linkage arm 190 passing therethrough and having its other end bent over one end of a latch 192 which is pivoted at point 194 to a clevis assembly 196 having an upper limit of movement for the latch 192 shown in the clevis by means of the dotted line 198. The front end of the latch 192 is notched to form a hook which engages in a slot or notch provided on a hub portion 200 of the adapter 172, thereby preventing inadvertent rotation, as is shown in FIG. 8. Thus, the casting chamber is locked in its upright position prior to initiation of its cycle.

When the solenoid is energized, the linkage arm 190 will move downward causing the latch 192 to pivot around the point 194 and permitting it to move to the upper limit 198 in the clevis 196. Simultaneously with the energization of the solenoid, the motor is caused to operate thereby rotating the shaft 184. By moving the latch upward, the adapter 172 is released and the shaft 184 will be free to rotate so that the casting chamber can be rotated from its upright position to its inverted position.

Also shown in the plate 180 of FIG. 7 is the fuse 130, a printed circuit board 202 which contains the relays 120 and 126, as well as the potentiometer 144 for controlling the vacuum timer and the potentiometer 158 for controlling the pressure timer. The two potentiometers provide the ability for varying the predetermined timing intervals of the two timers.

There has been disclosed heretofore the best embodiment of the invention presently contemplated. However, it is to be understood that various changes and modifications may be made thereto without departing from the spirit of the invention.

What is claimed is:

1. In a casting machine having a rotatable casting chamber capable of supporting therein an alloy filled, open-ended container and an investment casting ring having a sprue hole, such that the sprue hole in the casting ring faces the open end of the container, vacuum means for producing a vacuum in the casting chamber, pressure means for providing compressed air into the casting chamber and venting means for venting the casting chamber, the improvement comprising a casting control circuit including, energizing switch means for activating said vacuum means, vacuum timing means activated by said switch means for decoupling said vacuum means from said vacuum chamber after a predetermined first time interval, motor means connected to said casting chamber and activated by the termination of said first time interval to rotate said casting chamber to an inverted position, pressure timing means activated by the termination of said first timing interval to interconnect said pressure means to said casting chamber for a subsequent predetermined second time interval, said motor means being further activated by the termination of said second timing interval to return said casting chamber to its initial upright position, and reversing switch means activated by the termination of said second time interval for interconnecting said venting means to said casting chamber.

2. The improvement as in claim 1, and wherein said energizing switch means further includes a momentary contact switch interconnected to a power source, and a relay switch, said momentary contact switch energizing said relay switch such that it is maintained interconnected to the power source.

3. The improvement as in claim 2, and wherein said vacuum timing means is interconnected in series between said relay switch on the one hand, and said motor means and pressure timing means on the other hand, said vacuum timing means including a normally open switch which closes at the termination of said first time interval thereby energizing said pressure timing means and said motor means.

4. The improvement as in claim 3, and wherein said pressure timing means is interconnected in series between the power source and said motor means, said pressure timing means including a normally open switch which closes at the termination of said second timing interval thereby energizing said motor means.

5. The improvement as in claim 4, and wherein said casting control circuit further comprises first disconnect switch means serially interconnected between said vacuum timing means, said motor means and the power source, and second disconnect switch means serially interconnected between said pressure timing means, said motor means and the power source, both of said disconnect switch means being operatively coupled to said casting chamber whereby said first switch means disconnects the power source from said motor means when said casting chamber reaches its inverted position, and said second disconnect switch means disconnects the power source from said motor means when said casting chamber reaches its upright position.

6. The improvement as in claim 5, and wherein said disconnect switch means are microswitches comprising a cam follower trigger, and further comprising a cam surface rotatingly coupled to said casting chamber, said cam surface containing a single detent, whereby when either cam follower trigger engages the detent, the respective disconnect switch means is operated.

7. The improvement as in claim 2, and wherein the vacuum means includes a vacuum pump interconnected to a power source by a first relay switch and is coupled to the casting chamber through a first valve; the pressure means includes a source of compressed air which is coupled to the casting chamber by said first valve and is operated by a second relay switch, the second relay switch being connected in series with a turnover switch triggered as the casting chamber is turned from its initial upright position; and the venting means includes a second valve operated by a third relay switching coupling the casting chamber to the atmosphere, and wherein said control circuit further comprises means interconnecting the coils of said first, second and third relay switches to said self-holding relay switch to be energized thereby, whereby upon energization of said self-holding relay said first relay switch interconnects the vacuum pump to the power source and decouples the casting chamber from the atmosphere, and as the casting chamber is being inverted, the casting chamber is decoupled from the vacuum and coupled to the source of compressed air.

8. The improvement as in claim 7, and wherein said reversing switch means further comprises a reversing relay switch energized by said pressure timing means at the termination of said second time interval for de-energizing said self-holding relay switch whereby as the self-holding relay switch is de-energized the vacuum pump is disconnected from the power source and the casting chamber is coupled to the atmosphere.

9. The improvement as in claim 1, and wherein said control circuit further comprises brake means connected in parallel across said motor means for locking the casting chamber in its upright position prior to initiation of its cycle.

10. The improvement as in claim 9, and wherein said brake means further comprises a solenoid connected in parallel circuit arrangement with said motor means, clevis means, a latch member pivotally coupled to said clevis means, a linkage rod coupled between said solenoid and said latch member and operatively controlling the pivotal movement of said latch member by means of the energization of said solenoid, slot means for engagingly receiving said latch member when it is in a released position resulting from the de-energization of said solenoid, and disconnect switching means for respectively de-energizing said solenoid when the casting chamber reaches its inverted position and its upright position.

11. The improvement as in claim 1, and further comprising adjusting means for adjusting said first and second timing intervals.

12. A casting machine having a rotatable casting chamber capable of supporting therein an alloy filled, open-ended container and an investment casting ring having a sprue hole, such that the sprue hole in the casting ring faces the open end of the container, vacuum means for producing a vacuum in the casting chamber, pressure means for providing compressed air into the casting chamber, venting means for venting the casting chamber, energizing switch means for activating said vacuum means, vacuum timing means activated by said switch means for decoupling said vacuum means from said vacuum chamber after a predetermined first time interval, motor means connected to said casting chamber and activated by the termination of said first time interval to rotate said castiing chamber to an inverted position, pressure timing means activated by the termination of said first timing interval to interconnect said pressure means to said casting chamber for a subsequent predetermined second time interval, said motor means being further activated by the termination of said second timing interval to return said casting chamber to its innitial upright position, and reversing switch means activated by the termination of said second time interval for interconnecting said venting means to said casting chamber.

13. A casting machine as in claim 12, and wherein said energizing switch means further includes a momentary contact switch interconnected to a power source, and a self-holding relay switch, said momentary contact switch energizing said self-holding relay switch such that it is maintained interconnected to the power source.

14. A casting machine as in claim 13, and wherein said vacuum timing means is interconnected in series between said self-holding relay switch on the one hand, and said motor means and pressure timing means on the other hand, said vacuum timing means including a normally open switch which closes at the termination of said first time interval thereby energizing said pressure timing means and said motor means.

15. A casting machine as in claim 14, and wherein said pressure timing means is interconnected in series between the power source and said motor means, said pressure timing means including a normally open switch which closes at the termination of said second timing interval thereby energizing said motor means.

16. A casting machine as in claim 15, and further comprising first disconnect switch means serially interconnected between said vacuum timing means, said motor means and the power source, and second disconnect switch means serially interconnected between said pressure timing means, said motor means and the power source, both of said disconnect switch means being operatively coupled to said casting chamber whereby said first switch means disconnects the power source from said motor means when said casting chamber reaches its inverted position, and said second disconnect switch means disconnects the power source from said motor means when said casting chamber reaches its upright position.

17. A casting machine as in claim 16, and wherein said disconnect switches are microswitches comprising a cam follower trigger and further comprising a cam surface rotatingly coupled to said casting chamber, said cam surface containing a single detent, whereby when the cam follower triggers engage the detent the respective disconnect switch is operated.

18. A casting machine as in claim 12, and further comprising brake means connected in parallel across said motor means for locking the casting chamber in its initial position.

19. A casting machine as in claim 18, and wherein said brake means further comprises a solenoid connected in parallel circuit arrangement with said motor means, clevis means, a latch member pivotally coupled to said clevis means, a linkage rod coupled between said solenoid and said latch member and operatively controlling the pivotal movement of said latch member by means of the energization of said solenoid, slot means for engagingly receiving said by said latch member when it is in a released position resulting from the de-energization of said solenoid and disconnect switching means for respectively de-energizing said solenoid when the casting chamber reaches its inverted position and its upright position.

20. The improvement as in claim 12, and further comprising adjusting means for adjusting said first and second timing intervals.

\* \* \* \* \*